United States Patent [19]

Nedenskov et al.

[11] 3,954,813
[45] May 4, 1976

[54] FURANE DERIVATIVES AND PRODUCTION THEREOF

[75] Inventors: Poul Nedenskov, Birkerod; Karol Alster, Farum, both of Denmark

[73] Assignee: Aktieselskabet Grindstedvaerket, Arhus, Denmark

[22] Filed: June 19, 1974

[21] Appl. No.: 480,721

[52] U.S. Cl. ........................... 260/347.3; 260/347.5; 260/347.8; 260/999; 260/346.1 R
[51] Int. Cl.² ...................................... C07D 307/54
[58] Field of Search ...................... 260/347.3, 347.5

[56] References Cited
OTHER PUBLICATIONS

Holland et al., *Bull. Soc. Chim. Fr.*, p. 1699 (1971).
Dunlop et al., *The Furans*, pp. 42, 63, 262, 448–449, 455 & 466–467 (1953).
Hunsdiecker et al., *Chem. Abst.*, Vol. 37, Col. 3404–3405 (1943).
Novitskii et al., *Chem. Abst.*, Vol. 55, Col. 22277 (1961).
French Patent 1186346 Abstract, *Chem. Abst.*, Vol. 56, Col. 455 (1962).
Hillers et al., *Chem. Abst.*, Vol. 59, Col. 1564–1565 (1963).
Ponomarev et al., *Chem. Abst.*, Vol. 71, Item 124191 (1969).
Bel'skii et al. I, *Chem. Abst.*, Vol. 66, Item 75853 (1967).
Elix et al., *Chem. Abst.*, Vol. 66, Item 55298 (1967).
Buchta et al., I *Chem. Abst.*, Vol. 66, Item 28595 (1967).
Buchta et al., II, *Chem. Abst.*, Vol. 63, Col. 11344–11345 (1965).
Bel'skii et al. II, *Igv. Akad. Nank SSSR, Ser. Khim*, pp. 2338–2343 (1970).
Abbott et al., *Chem. Phys. Lipids*, Vol. 4, pp. 351–366 (1970).

*Primary Examiner*—Harry I. Moatz
*Attorney, Agent, or Firm*—Lawrence Rosen; E. Janet Berry

[57] ABSTRACT

This invention relates to therapeutically active 2,5-furane derivatives, wherein the substituent in the 2-position is a lower alkyl group or a group ROOC—$(CH_2)_7$—, in which R is hydrogen or lower alkyl, the 5-substituent being an alkyl or alkylene group of 4 to 13 carbon atoms, which may be substituted with an oxygen atom, a hydroxy group or a lower alkyl group at the third carbon atom, counted from the furane ring, and to the production thereof.

7 Claims, No Drawings

FURANE DERIVATIVES AND PRODUCTION THEREOF

This invention relates to new 2,5-furane derivatives and their production and to intermediates in the said production.

The new furane derivatives of the invention are represented by the following formula

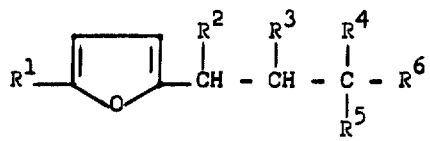

wherein $R^1$ represents a lower alkyl group or a group of the formula $ROOC-(CH_2)_7-$, wherein R represents hydrogen or a lower alkyl group, each of $R^2$ and $R^3$ represents hydrogen, or $R^2$ and $R^3$ together represent a further bond between the carbon atoms, each of $R^4$ and $R^5$ represents hydrogen, hydroxy or a lower alkyl group, or $R^4$ and $R^5$ together represent an oxygen atom, and $R^6$ represents a group $C_nH_{2n+1}$, n being an integer from 1–10.

The lower alkyl groups of the present compounds are preferably those having 1–4 carbon atoms, i.e. methyl, ethyl, propyl, isopropyl, butyl, isobutyl, and tert.butyl. The $R^6$ group is preferably a pentyl group.

The compounds of the invention have useful biological properties combined with a relatively low toxicity. Thus, they have a controlling effect upon the hormone production of corpus luteum, and are in that respect almost as effective as the prostaglandine $PGF_{2\alpha}$ without, however, showing any side effects.

The following schemes of reaction illustrate the production of the compounds of the invention:

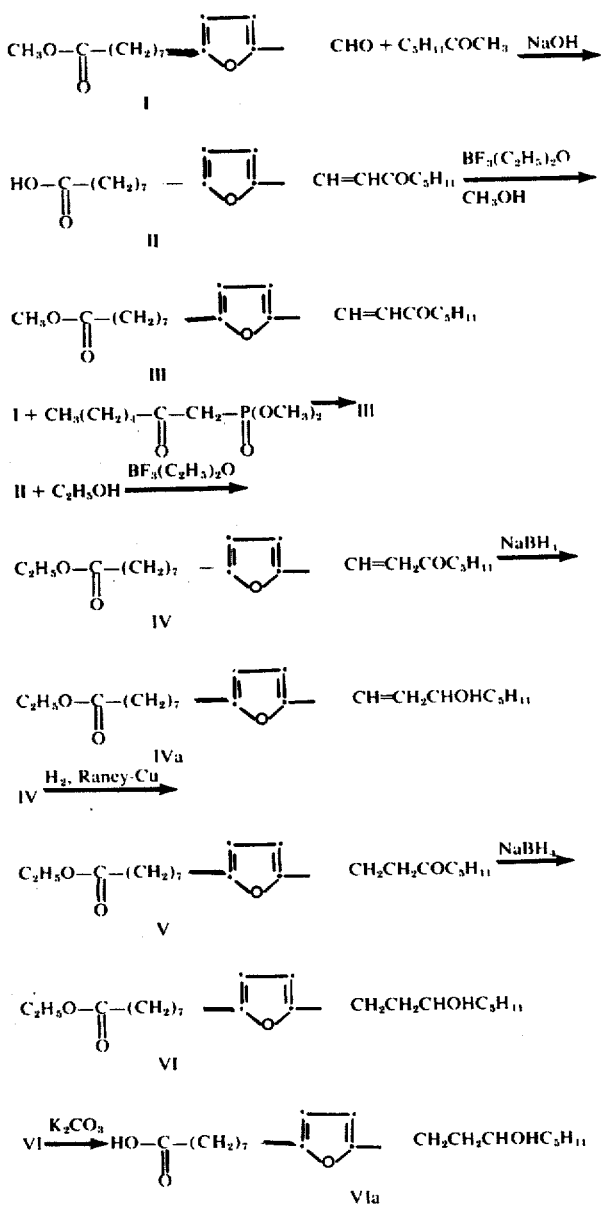

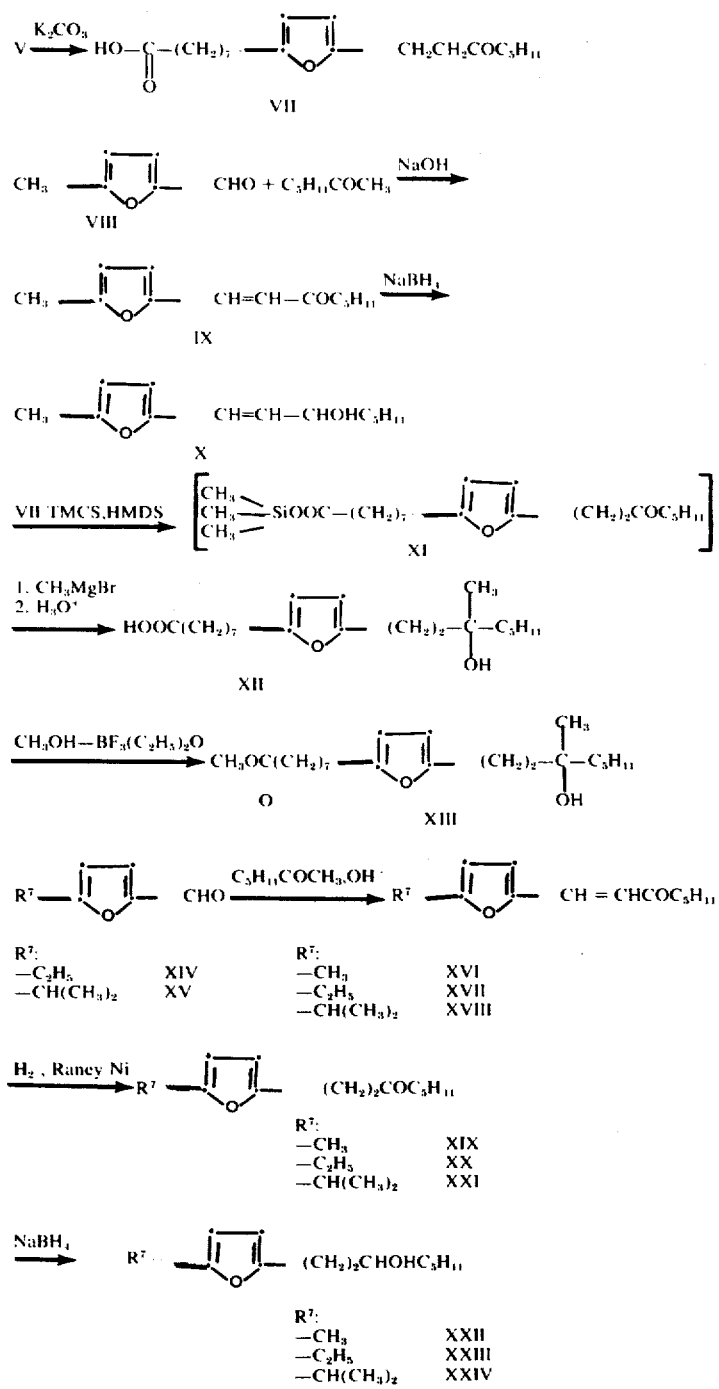
The starting materials for the production of the compounds of the invention are furane derivatives of the formula
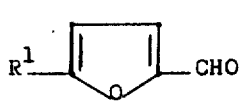
wherein $R^1$ is as hereinbefore defined, which can be produced from known compounds of the formula
for example by formylating according to Vilsmeyer.

The starting aldehydes are condensed with the appropriate alkan-2-one, e.g. 2-heptanone, or a 2-oxoalkyl-phosphonic acid dimethyl ester to establish a 3-oxy-1-alkenyl group at the 5-position of the furane ring and optionally hydrogenating at the double bond in 1-position of said side chain catalytically, and reducing the keto group with sodium boronhydride or subjecting the keto group to a Grignardation using an alkylmagnesium halide as the Grignard reagent.

When $R^1$ represents the group $ROOC-(CH_2)_7-$, wherein R is hydrogen, the carboxyl group may subsequently be esterified to yield esters of the invention or, if the resulting compound is an ester, it may be saponified to yield the corresponding acid.

The introduction of the side chain in 5-position is preferably carried out at room temperature in solution in an alkanol, e.g. methanol or ethanol.

Suitable catalysts for the hydrogenation are Raney nickel, Raney copper, and noble metal catalysts, e.g. palladium.

The following examples are illustrative of the production of the present compounds, the various compounds being identified by the numbering in the above schemes of reaction.

EXAMPLE 1

8-[5-(3-Oxo-1-octenyl)-2-furyl]-octanoic acid (II)

I (9.17 g, 0.0364 mole), produced by formylating furyl-2-octanoic acid, was dissolved in methanol (60 ml), and the solution was cooled to −5°C. Aqueous 20% sodium hydroxide (9.1 g) was added in one portion with stirring. To the resulting mixture, 2-heptanone (5.05 g, 0.0444 mole) was added with stirring over a period of 10 minutes at a temperature of 18°-20°C. The stirring was continued for one hour at the same temperature, and then for additional 16 hours at room temperature. The reaction mixture was poured into water (130 ml) and adjusted to pH 7.2 with 3N acetic acid (9.2 ml). The resulting yellow crystals were isolated by filtration and washed with water (30 ml). The filtrate (F) was collected. The wet cake of crystals was suspended in a mixture of water (80 ml) and ether (80 ml) and stirred. The resulting emulsion was neutralized to pH 7 with 3N acetic acid. The ethereal layer was separated. The aqueous layer was extracted with ether (50 ml). The combined ethereal extracts were washed with water (50 ml) and then dried over magnesium sulfate. The dried ethereal solution was evaporated to dryness from a water bath (60°C), at last under 15 mm Hg. 6.21 g of crude II were hereby obtained as a yellow oil, which solidified at room temperature.

The above filtrate (F) was stirred with ether (50 ml) and the pH of the emulsion was adjusted to 7 with 3N acetic acid. The ethereal layer was separated, and the aqueous layer extracted with ether (50 ml). The combined ethereal extracts were washed with water (50 ml), dried over magnesium sulfate, and the ether removed by distillation from a water bath (60°C), at last under 15 mm Hg. Chromatography of the yellow, oily residue (5.30 g) on silica gel (150 g, 60-120 mesh, from BDH Chemicals Ltd.) and elution with increasing concentration of acetone in n-hexane gave 2.20 g of crude II.

The combined crude products were crystallized from n-hexane (250 ml). 7.45 g (61%) of II were hereby obtained as pale, yellow crystals, m.p. 58°-59°C.

Calculated for $C_{20}H_{30}O_4$ (334.4): C 71.8, H 9.0
Found: C 71.7, H 9.0

EXAMPLE 2

8-[5-(3-Oxo-1-octenyl)-2-furyl]-octanoic acid methyl ester (III)

A. II (2.52 g, 0.00755 mole), methanol (30 ml), and ethyl ether-borontrifluoride complex (0.24 g) were stirred and heated under reflux for 1 hour. After cooling, the reaction mixture was poured into ice-water (150 ml) and extracted with two 80-ml portions of ether. The combined ethereal extracts were washed with cold 10% sodium carbonate (50 ml) and then with two 50-ml portions of cold water. The ethereal solution was dried over magnesium sulfate and evaporated to dryness from a water bath (60°C), at last under 15 mm Hg. Distillation under nitrogen of the residual oil (2.46 g) gave 2.07 g (79%) of III, $b_{0.3}$ 202°-204°C, $n_D^{25}$ 1.5262.

Calculated for $C_{21}H_{32}O_4$ (348.5): C 72.4, H 9.3 one $OCH_3$ 8.9 Found: C 72.5, H 9.2 $OCH_3$ 8.9

B. 50% sodium hydride in mineral oil (0.96 g, 0.02 mole) was suspended in dry 1,2-dimethoxyethane (200 ml). The slurry was cooled to 15°C and stirred vigorously with a mechanical stirrer. (2-Oxoheptyl)-phosphoric acid dimethyl ester (Wadsworth et al: J.A.C.S. 83 (1961) 1733) (4.44 g, 0.02 mole) was added dropwise over a period of 30 minutes, the reaction temperature being kept at 15°-20°C. After the addition, the suspension of a white, voluminous precipitate was stirred for 1 hour at room temperature. A solution of I (5.04 g, 0.02 mole) in 1,2-dimethoxyethane (30 ml) was added dropwise over a period of 30 minutes to the stirred suspension, maintained below 25°C. The resulting turbid, yellow solution was stirred at room temperature for 1.5 hours. The solvent (200 ml) was distilled off from a water bath (70°C) under reduced pressure (40 mm Hg). After cooling, the oily residue was diluted with cold water (300 ml) and extracted with two 200-ml portions of ether. The combined ethereal extracts were washed with two 100-ml portions of water and then dried over magnesium sulfate. The dried ethereal solution was evaporated to dryness from a water bath (60°C), at last under 15 mm. The residual yellow oil was purified by distillation under nitrogen. 6.34 g (91%) of III was hereby obtained as a yellow liquid, $b_{0.1}$ 194°-200°C, $n_D^{25}$ 1.5256. In tlc it has the same $R_f$ values in different solvents as the compound obtained by method A.

EXAMPLE 3

8-[5-(3-Oxo-1-octenyl)-2-furyl]-octanoic acid ethyl ester (IV)

A mixture of II (9.94 g, 0.0298 mole), ethanol (190 ml), and ethyl ether-borontrifluoride complex (0.97 g) was stirred and heated under reflux for 1.5 hours. After cooling, the reaction mixture was poured into ice-water (600 ml) and extracted with three 300-ml portions of ether. The combined ethereal extracts were washed with cold 10% sodium carbonate (100 ml) and then with two 200-ml portions of cold water. The ethereal solution was dried over magnesium sulfate and evaporated to dryness from a water bath (60°C), at last under 15 mm Hg. The residual yellow oil (9.84 g) was purified by distillation under nitrogen from a potassium acetatecoated flask giving 8.57 g (79%) of IV, $b_{0.2}$ 198°-201°C, $n_D^{25}$ 1.5217.

Calculated for $C_{22}H_{34}O_4$ (362.5): C 72.9, H 9.5, $OC_2H_5$ 12.4 Found: C 73.0, H 9.5, $OC_2H_5$ 12.3

EXAMPLE 4

8-[5-(3-Oxooctyl)-2-furyl]-octanoic acid ethyl ester (V)

IV (1.74 g, 0.0048 mole), ethanol (25 ml), and Raney copper (Ponomarev et al., J.Gen.Chem. USSR 30 (1960) 584) (0.75 g) were shaken under 80 atmospheres of hydrogen for 6 hours at 30°C. After filtration, the ethanol was distilled under reduced pressure from a water bath (60°C). Ether (30 ml) was added to the residue, and the turbid solution was filtered (G4, Celite). The ethereal solution was evaporated to dryness from a water bath (50°C) under reduced pressure, at last under 15 mm Hg. The residual oil was purified by distillation under nitrogen. 1.51 g (86%) of V was hereby obtained as an almost colorless oil, $b_{0.2}$ 178°–181°C, $n_D^{25}$ 1.4700.

Calculated for $C_{22}H_{36}O_4$ (364.5): C 72.5, H 10.0, $OC_2H_5$ 12.4 Found: C 72.3, H 10.0, $OC_2H_5$ 12.4

EXAMPLE 5

8-[5-(3-Hydroxyoctyl)-2-furyl]-octanoic acid ethyl ester (VI)

V (1.25 g, 0.00343 mole) was dissolved in absolute ethanol (70 ml), and the solution was cooled to −5°C. Sodium tetrahydroborate (0.50 g, 0.0132 mole) was added portionswise during 3 minutes with stirring. The turbid solution was stirred at 0°–5°C for 15 minutes, then at room temperature for 1 hour. The colorless solution was poured into ice-water (250 ml). 1.5 N sodium hydroxide (10 ml) was added with stirring to the resulting emulsion. The stirring was continued for 15 minutes. The white emulsion was extracted with three 100-ml portions of ether. The combined ethereal extracts were washed with cold water (100 ml), dried over magnesium sulfate, and the solvent was removed by distillation from a water bath (60°C), at last under 15 mm Hg. Distillation of the residual oil (1.34 g) gave 1.18 g (94%) of VI as a colorless oil, $b_{0.1}$ 172°–175°C, $n_D^{25}$ 1.4731.

Calculated for $C_{22}H_{38}O_4$ (366.5): C 72.1, H 10.5, $OC_2H_5$ 12.3 Found: C 72.2, H 10.5, $OC_2H_5$ 12.4

EXAMPLE 6

8-[5-(3-Oxooctyl)-2-furyl]-octanoic acid (VII)

A mixture of V (5.10 g, 0.014 mole), methanol (180 ml), and 20% potassium carbonate (60 g) was stirred and heated under reflux for 1 hour. The turbid solution was concentrated to ¼ of the volume by distillation from a water bath (60°C) under reduced pressure (60 mm Hg). The residue was diluted with water (300 ml), and the resulting clear solution was acidified to pH 6 with acetic acid. The emulsion was extracted with two 150-ml portions of ether. The combined ethereal extracts were washed with two 100-ml portions of water, and then dried over magnesium sulfate. Ether was distilled off from a water bath (60°C), at last under 15 mm Hg. The yellow, oily residue (4.62 g) solidified at room temperature. Purification by crystallization from n-hexane (40 ml) gave 3.54 g (75%) of VII as slightly yellow crystals, m.p. 64°–65°C.

Calculated for $C_{20}H_{32}O_4$ (336.5): C 71.4, H 9.6 Found: C 71.2, H 9.6

EXAMPLE 7

1-(5-Methyl-2-furyl)-1-octen-3-ol (X)

The starting material, 1-(5-methyl-2-furyl)-1-octen-3-one (IX), which is known (Chem.Abstr. 74 (1971) 141,418 g), was prepared from VIII (J.Org.Chem. 22 (1957) 1269) after the directions given in the literature (J.A.C.S. 70 (1948) 2695).

IX (1.65 g, 0.008 mole) was dissolved in absolute ethanol (200 ml), and the solution was cooled to 0°C. Sodium tetrahydroborate (0.70 g, 0.0185 mole) was added in one portion with stirring. The turbid solution was stirred at 0°–5°C for 15 minutes and then at room temperature for 20 hours. The solution was concentrated to ¼ of the volume by distillation from a water bath (40°C) under reduced pressure (50 mm Hg). The residual solution was cooled to 10°C, and then cold water (800 ml) and N sodium hydroxide (25 ml) were added successively with stirring. The stirring was continued for 15 minutes at room temperature and then the pH of the emulsion was adjusted to 7.8 by addition of 3N acetic acid. The reaction mixture was extracted with two 150-ml portions of ether. The combined organic extracts were washed with water (100 ml) and dried over magnesium sulfate. The ethereal solution was evaporated to dryness from a water bath (60°C) under reduced pressure, at last under 15 mm Hg. The residual oil (1.67 g) was purified by distillation under nitrogen. 1.13 g (68%) of X were hereby obtained as a yellow liquid, $b_{0.2}$ 97°–99°C, $n_D^{20}$ 1.5166.

EXAMPLE 8

8-[5-(3-Hydroxyoctyl)-2-furyl]-octanoic acid (VIa)

A mixture of VI (2.73 g, 0.00745 mole), methanol (100 ml), and 20% aqueous potassium carbonate solution (30 ml) was stirred and heated under reflux for 1 hour. The turbid solution was concentrated to ¼ of the volume by distillation from a water bath (60°C) under reduced pressure (60 mm Hg). The residue was diluted with water (100 ml) and adjusted to pH 7 with acetic acid (2.7 ml). The resulting emulsion was extracted with two 80-ml portions of ether. The combined ethereal extracts were washed with water (100 ml) and then dried over magnesium sulfate. Ether was distilled off from a water bath (50°C), at last under 15 mm Hg. The yellow, oily residue (2.58 g) was purified by crystallization from petroleum ether (boiling below 50°C) (450 ml). 2.13 g (84%) of VIa were hereby obtained as almost white crystals with m.p. 43°–45°C.

Calculated for $C_{20}H_{34}O_4$ (338.5): C 71.0 H 10.1 Found: C 70.8 H 10.1

EXAMPLE 9

8-[5-(3-Oxooctyl)-2-furyl]-octanoic acid methyl ester

III (11.37 g, 0.0326 mole), methanol (150 ml), and Raney nickel (2.5 g) were stirred at room temperature under 1 atmosphere of hydrogen, until one molequivalent of hydrogen had reacted. After filtration, the solvent was removed by distillation from a water bath (60°C) under reduced pressure, at last under 15 mm Hg. The residual, light yellow oil (11.4 g) was purified by preparative tlc (thin layer chromatography) on silica gel (mixture of petroleum ether (b.<50°C) and ether (2:1) as eluent). 7.25 g of the title compound were obtained as a yellowish oil. Further purification by distillation under nitrogen gave 7.05 g (62%) of the title compound as an almost colourless oil, $b_{0.07}$ 172°–180°C, $n_D^{25}$ 1.4723.

Calculated for $C_{21}H_{34}O_4$ (350.5): C 72.0, H 9.8, $OCH_3$ 8.8 Found: C 71.8, H 9.9, $OCH_3$ 9.0

EXAMPLE 10

8-[5-(3-Hydroxyoctyl)-2-furyl]-octanoic acid methyl ester

The ester of Example 9 (1.61 g, 0.0046 mole) was dissolved in methanol (30 ml), and sodium tetrahydroborate (0.80 g, 0.021 mole) was added at −10°C with stirring. The stirring was continued for 90 minutes, the temperature of the reaction mixture increasing to 22°–25°C. The resulting solution was poured into ice-water (200 ml). 1.5N aqueous sodium hydroxide solution (10 ml) was then added, and the emulsion was stirred for 15 minutes. The reaction mixture was extracted with three 100-ml portions of ether. The combined organic extracts were washed with two 100-ml portions of water and dried over magnesium sulfate. The ethereal solution was evaporated to dryness from a water bath (60°C) under reduced pressure (15 mm Hg). The residual oil (1.59 g) was purified by distillation under nitrogen. 1.50 g (93%) of the title compound were obtained as a colourless oil, $b_{0.07}$ 176°–178°C, $n_D^{25}$ 1.4759.

Calculated for $C_{21}H_{36}O_4$ (352.5): C 71.6, H 10.3, $OCH_3$ 8.8 Found: C 71.7, H 10.5, $OCH_3$ 8.7

EXAMPLE 11

8-[5-(3-Hydroxyoctyl)-2-furyl]-octanoic acid

A mixture of the ester of Example 10 (2.73 g, 0.0077 mole), methanol (100 ml), and 20% potassium carbonate (30 ml) was stirred and heated under reflux for one hour. The colourless solution was concentrated to one fourth of the original volume by distillation from a water bath (60°C) under reduced pressure (60 mm Hg). The residue was diluted with water (100 ml), and the resulting turbid solution was acidified to pH 6 with acetic acid. The emulsion was extracted with two 100-ml portions of ether. The combined ethereal extracts were washed with two 100-ml portions of water and then dried over magnesium sulfate. Ether was distilled off on a water bath (60°C), at last under 15 mm Hg. The yellow, oily residue (2.58 g) solidified at 10°C. Purification by crystallization from petroleum ether (b.<50°C) (450 ml) gave 2.13 g (81%) of the title compound as white crystals with m.p. 43°–45°C.

Calculated for $C_{20}H_{34}O_4$ (338.5): C 71.0, H 10.1 Found: C 70.8, H 10.1

EXAMPLE 12

8-[5-(3-Hydroxy-3-methyloctyl)-2-furyl]-octanoic acid methyl ester (XIII)

VII (4.50 g, 0.0133 mole), pyridine (25 ml), hexamethyldisilazan (HMDS) (7.2 ml), and trimethyl silylchloride (TMCS) (2.4 ml) were mixed, and the mixture was left overnight protected from moisture. The suspension was then filtered in a dry atmosphere, and the filtrate was evaporated on a water bath (80°C) under reduced pressure (10 mm Hg). The residue was mixed with dry ether (50 ml), and the mixture was filtered to remove a small amount of insoluble material. The filtrate was cooled to 2°C in a dry nitrogen atmosphere, and a 3.7M ethereal solution of methyl magnesium bromide (7.8 ml, 0.0289 mole) was added dropwise with stirring over a period of 25 minutes at about 10°C. The resulting suspension was stirred overnight at room temperature. It was then added to a mixture of N HCl (32 ml) and water (120 ml), the temperature of which was 5°C, and the resulting mixture was stirred for 90 minutes. The ethereal layer was then separated, and the aqueous phase was extracted with ether (30 ml). The combined ethereal extracts were extracted with 0.5N aqueous sodium hydroxide (40 ml). The aqueous extract was made acidic with 0.5N hydrochloric acid (42 ml) and extracted with two 25-ml portions of ether. The combined ethereal extracts were dried with magnesium sulfate and evaporated to dryness from a water bath (70°C), at last under 15 mm Hg. The residual crude acid XII (4.23 g) was esterified in a mixture of methanol (50 ml) and ethyl ether - borontrifluoride complex (0.5 ml) as described in Example 2 to give the crude methyl ester XIII (4.2 g). This crude ester was purified by chromatography using a column of silica gel and petrol ether - ether (1:1) as eluent to give 2.1 g of crude oil. The distillation under nitrogen of this crude oil gave 1.83 g (37%) of XIII, $b_{0.3}$ 178°–180°C, $n_D^{25}$ 1.4749.

Calculated for $C_{22}H_{38}O_4$ (366.5): C 72.1, H 10.5, $OCH_3$ 8.5 Found: C 71.5, H 10.4, $OCH_3$ 8.6

The NMR spectrum was in accordance with the presumed structure for XIII.

EXAMPLE 13

8-[5-(3-Hydroxy-3-methyloctyl)-2-furyl]-octanoic acid (XII)

A mixture of XIII (0.91 g, 0.0025 mole), methanol (10 ml), and 20% potassium cabonate (5 ml) was stirred and refluxed for 90 minutes. The clear yellow solution was mixed with water (15 ml) and acidified to pH 5–6 with acetic acid. The emulsion was extracted with two 15-ml portions of ether. The combined ethereal extracts were dried over magnesium sulfate. Ether was distilled off from a water bath (60°C), at last under 0.1 mm Hg. The yellow, oily residue (0.86 g) was purified by chromatography on three 20 × 20 cm preparative tlc plates (Merck silica gel $60F_{254}$—2 mm layer), and the isolated crude XII herefrom was distilled at 175°–185°C and 0.03 mm Hg to give 0.63 g XII (71%) as a light yellow oil, $n_D^{25}$ 1.4844.

Calculated for $C_{21}H_{36}O_4$ (352.5): C 71.6, H 10.3 Found: C 71.7, H 10.3

EXAMPLE 14

1-(5-Alkyl-2-furyl)-octen-3-ones (XVII, XVIII)

To the stirred solution of a 5-alkylfuraldehyde (0.0666 mole) and 2-heptanone (9.3 ml, 7.58 g, 0.0666 mole) in methanol (25 ml) aqueous 20% sodium hydroxide (1.8 ml) was added dropwise at 10°–12°C over a period of 10 minutes. The clear yellow solution was stirred at the same temperature for 1 hour, then for 18 hours at room temperature. The pH of the resulting mixture was adjusted to 7 by addition of acetic acid. The reaction mixture was poured into water (100 ml) and extracted with two 70-ml portions of ether. The combined organic extracts were washed with three 50-ml portions of ether and dried over magnesium sulfate. The ethereal solution was evaporated to dryness from a water bath (70°C) under reduced pressure, at last under 15 mm Hg. The residual oil was purified by distillation under 10 mm Hg.

| R | $b_{10\,mm}$ °C | $n_D^{25}$ | m. °C | yield % |
|---|---|---|---|---|
| $C_2H_5$ | 166–174 | | 41 | 64 |
| $CH(CH_3)_2$ | 174–182 | 1.5415 | | 57 |

| R | formula | molecular weight | calculated C | H | found C | H |
|---|---|---|---|---|---|---|
| $C_2H_5$ | $C_{14}H_{28}O_2$ | 220.3 | 76.3 | 9.2 | 76.2 | 9.2 |
| $CH(CH_3)_2$ | $C_{15}H_{22}O_2$ | 234.3 | 76.9 | 9.5 | 76.6 | 9.4 |

EXAMPLE 15

1-(5-Alkyl-2-furyl)-3-octanones (XIX-XXI)

A 1-(5-alkyl-2-furyl)-1-octen-3-one (0.03 mole), methanol (150 ml), and Raney nickel (10% by weight of the olefin) were stirred at room temperature under 1 atmosphere of hydrogen, until one molequivalent of hydrogen had reacted. After filtration, the solvent was removed by distillation from a water bath (60°C) under reduced pressure, at last under 15 mm Hg. The residual light yellow oil was purified by preparative thin layer chromatography. Silica gel has been used as adsorbent and a mixture of ether and petroleum ether (b.<50°C) (1:8) as developing solvent. The adsorbent was scraped off the glass plates and stirred for 1 hour with ether. After filtration, the solution was evaporated to dryness from a water bath (60°C) under reduced pressure, at last under 15 mm Hg. The residual oil was purified by distillation under reduced pressure.

| R | $b_{10\,mm}$ °C | $n_D^{25}$ | (°C) | yield % |
|---|---|---|---|---|
| $CH_3$ | 140–142 | 1.4687 | | 71 |
| $C_2H_5$ | 147–150 | 1.4675 | | 86 |
| $CH(CH_3)_2$ | 158–159 | 1.4651 | | 71 |

| R | formula | molecular weight | calculated C | H | found C | H |
|---|---|---|---|---|---|---|
| $CH_3$ | $C_{13}H_{20}O_2$ | 208.3 | 75.0 | 9.7 | 74.3 | 9.8 |
| $C_2H_5$ | $C_{14}H_{22}O_2$ | 222.3 | 75.6 | 10.0 | 75.5 | 10.1 |
| $CH(CH_3)_2$ | $C_{15}H_{24}O_2$ | 236.3 | 76.2 | 10.2 | 76.1 | 10.3 |

EXAMPLE 16

5-Alkyl-α-pentyl-2-furanpropanols (XXII-XXIV)

A 1-(5-alkyl-2-furyl)-3-octanone (XIX-XXI) (0.015 mole) was dissolved in ethanol (90 ml), and sodium tetrahydroborate (2.40 g, 0.064 mole) was added at −10°C with stirring. The stirring was continued for 90 minutes, the temperature of the reaction mixture increasing to 23°–25°C. The colourless solution was poured into ice-water (300 ml). 1.5N aqueous sodium hydroxide (20 ml) was then added, and the emulsion was stirred for 10 minutes. The reaction mixture was extracted with three 100-ml portions of ether. The combined organic extracts were washed with two 100-ml portions of water and dried over magnesium sulfate. The ethereal solution was evaporated to dryness from a water bath (60°C) under reduced pressure, at last under 15 mmHg. The residual oil was purified by distillation under reduced pressure.

| R | $b_{10\,mm}$ °C | $n_D^{25}$ | | yield % |
|---|---|---|---|---|
| $CH_3$ | 148–160 | 1.4744 | (20°C) | 95 |
| $C_2H_5$ | 152–155 | 1.4725 | | 93 |
| $CH(CH_3)_2$ | 160 | 1.4701 | | 91 |

| R | formula | molecular weight | calculated C | H | found C | H |
|---|---|---|---|---|---|---|
| $CH_3$ | $C_{13}H_{22}O_2$ | 210.3 | 74.2 | 10.5 | 74.1 | 10.5 |
| $C_2H_5$ | $C_{14}H_{24}O_2$ | 224.3 | 75.0 | 10.8 | 74.8 | 10.7 |
| $CH(CH_3)_2$ | $C_{15}H_{26}O_2$ | 238.4 | 75.6 | 11.0 | 75.4 | 11.2 |

We claim:

1. A 2,5-Furane derivative of the formula

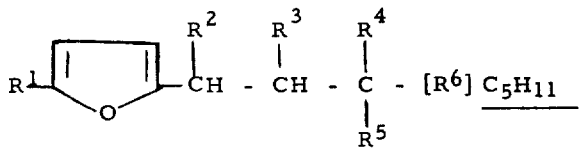

wherein $R^1$ represents a group of the formula $ROOC-(CH_2)_7$, wherein R represents hydrogen or a lower alkyl group, each of $R^2$ and $R^3$ represents hydrogen, or $R^2$ and $R^3$ together represent a further bond between the carbon atoms, and each of $R^4$ and $R^5$ represents hydrogen, hydroxy or a lower alkyl group, or $R^4$ and $R^5$ together represent an oxygen atom.

2. A compound of claim 1, in which R is an alkyl group of 1–4 carbon atoms.

3. A compound of claim 1, in which $R^1$ is $HOOC-(CH_2)_7-$, and esters thereof with alkanols of 1–4 carbon atoms.

4. A compound of claim 1, in which $R^1$ is $HOOC-(CH_2)_7-$, $R^2$ and $R^3$ are hydrogen, and $R^4$ and $R^5$ together are oxygen, and esters thereof with alkanols of 1–4 carbon atoms.

5. A compound of claim 1, in which $R^1$ is $HOOC-(CH_2)_7-$, $R^2$ and $R^3$ together are a further bond between the carbon atoms, and $R^4$ and $R^5$ together are oxygen, and the esters thereof with $C_1$-$C_4$ alkanols.

6. A compound of claim 1, in which $R^1$ is $HOOC-(CH_2)_7-$, $R^2$, $R^3$ and $R^4$ are hydrogen, and $R^5$ is hydroxy, and esters thereof with $C_1$-$C_4$ alkanols.

7. A compound of claim 1, in which $R^1$ is $HOOC-(CH_2)_7-$, $R^2$ and $R^3$ are hydrogen, $R^4$ is methyl, and $R^5$ is hydroxy, and esters thereof with $C_1$-$C_4$ alkanols.

* * * * *